US006117993A

United States Patent [19]
Iyer et al.

[11] Patent Number: 6,117,993
[45] Date of Patent: Sep. 12, 2000

[54] SYNTHONS FOR OLIGONUCLEOTIDE SYNTHESIS

[75] Inventors: Radhakrishnan P. Iyer, Shrewsbury; Dong Yu; Mao-Jun Guo, both of Somerville; Sudhir Agrawal, Shrewbury, all of Mass.

[73] Assignee: Hybridon, Inc., Milford, Mass.

[21] Appl. No.: 09/015,472

[22] Filed: Jan. 29, 1998

Related U.S. Application Data

[63] Continuation-in-part of application No. 08/457,198, Jun. 1, 1995, abandoned, application No. 08/597,434, Feb. 8, 1996, abandoned, and application No. 08/448,131, May 23, 1995, Pat. No. 5,750,674.

[51] Int. Cl.[7] ............................. C07H 19/04; C07H 19/20
[52] U.S. Cl. .................. 536/26.7; 536/25.33; 536/25.34
[58] Field of Search ............................... 536/26.7, 25.33, 536/25.34

[56] References Cited

U.S. PATENT DOCUMENTS

| | | | |
|---|---|---|---|
| 4,689,320 | 8/1987 | Kaji et al. | 514/44 |
| 4,806,463 | 2/1989 | Goodchild et al. | 435/5 |
| 5,107,065 | 4/1992 | Shewmaker et al. | 800/298 |
| 5,149,798 | 9/1992 | Agrawal et al. | 536/25.3 |
| 5,194,428 | 3/1993 | Agrawal et al. | 514/44 |
| 5,359,052 | 10/1994 | Stec et al. | 536/26.7 |
| 5,506,212 | 4/1996 | Hoke et al. | 514/44 |
| 5,512,668 | 4/1996 | Stec et al. | 536/25.33 |
| 5,614,622 | 3/1997 | Iyer et al. | 536/25.33 |
| 5,646,267 | 7/1997 | Stec et al. | 536/25.33 |
| 5,750,674 | 5/1998 | Iyer et al. | 536/26.7 |

FOREIGN PATENT DOCUMENTS

| | | |
|---|---|---|
| WO 94/17091 | 8/1994 | WIPO . |
| WO 95/09236 | 4/1995 | WIPO . |

OTHER PUBLICATIONS

Zon, "Oligonucleotide Analogues as Potential Chemotherapeutic Agents," *Pharmaceutical Research*, 5(9), 539–549 (1988).
Farquhar et al., "Synthesis and Biological Evaluation of Neutral Derivatives of 5–Fluoro–2–'deoxyurdine 5'–Phosphate," *J. Medicinal Chem.*, 26(8), 1153–1158 (Aug. 1983).
Iyer et al., "A Novel Nucleoside Phosphoramidite Synthon Derived From 1 R, 2 S–Ephredrine," *Tetrahedron: Asymmetry*, 6(5), 1051–1054 (May 1995).
Wang et al., "A Stereoselective Synthesis of Dinucleotide Phosphonothioate Triesters Through a Chiral Indol–oxazaphosphorine Intermediate," *Tetrahedron Letters*, 38(5), 705–708 (Feb. 3, 1997).
Krazewski et al., "Studies on Reactions of Nucleoside H–Phosphanates with Bifunctional Reagents. Part 1. Reactions with Amino Alcohols," *J. Chem. Soc., Perkin Trans. 1*, (No. 14), 1699–1704 (Jul. 21, 1993).
Jones et al., "Synthesis of Some Nucleoside Cyclic Phosphoramidates and Related Compounds Via Phosphoramidites," *J. Chem. Soc., Perkin Trans. 1*, (No. 2), 199–202 (Feb. 1985).
Kant et al., "Studies toward Structure–Activity Relationships of Taxol®: Synthesis and Cytotoxicity of Taxol® Analogues with C–2' Modified Phenylisoserine Side Chains," *Bioorganic and Medicinal Chem. Letters*, 3(11), 2471–2474 (1993).
Zamecnik et al., *Proc. Natl. Acad. Sci.* USA 75, 280–284 (1978).
Agrawal, *Trends In Biotech.*, 10, 152 (1992).
Chang and Pettitt, *Proc. Biophys. Molec. Biol.*, 58, 225 (1992).
Uhlmann and Peyman, *Chem. Rev.*, 90, 543 (1990).
Stein and Cheng, *Science*, 261, 1004 (1993).
Agrawal and Tang, *Antisense Res. And Dev.*, 2, 261 (1992).
Bayever et al., *Antisense Res. And Dev.*, 3, 383 (1993).
Stec and Wilk, *Angew–Chem. Int. Ed. Engl.*, 33, 709 (1994).
Lesnikowski, *J. Bioorg. Chem.*, 21, 127 (1993).
Stec et al., *J. Am. Chem. Soc.* 106, 6077 (1984).
Iyer et al., *J. Am. Chem. Soc.*, 112, 1253 (1990).
Iyer et al., *J. Am. Chem. Soc.*, 55, 4693 (1990).
Storey et al., *Nucleic Acids Res.*, 19, 4109 (1991).
Robertson et al., *J. Virology*, 54, 651 (1985).
Harris et al., *J. Virology*, 36, 659 (1980).
Rice et al., *Science*, 229, 726 (1985).
Davison and Scott, *J. Gen. Virology* 67, 2279 (1986).
Richards et al., *Virology*, 89, 395 (1978).
Miller and Purcell, *Proc. Natl. Acad. Sci.*, 87, 2057 (1990).
Simmonds et al., *J. Gen. Virol.*, 74 661–668 (1993).
Campbell et al., *Nature*, 311 350 (1984).

(List continued on next page.)

*Primary Examiner*—L. Eric Crane
*Attorney, Agent, or Firm*—McDonnell Boehnen Hulbert & Berghoff

[57] ABSTRACT

The invention provides new reagents and processes for synthesizing oligonucleotides, including stereoselective oligonucleotide synthesis. In a first aspect, the invention provides novel monomer synthons for the synthesis of oligonucleotides. Monomer synthons according to this aspect of the invention are useful in the synthesis of oligonucleotides and can be used in place of the well known beta-cyanoethyl phosphoramidite monomer synthon in the phosphoramidite synthesis procedure. Certain monomer synthons according to this aspect of the invention are useful in this procedure for producing oligonucleotides having defined stereochemistry.

In a second aspect, the invention provides processes for synthesizing monomer synthons according to the invention, including diastereomerically enriched or purified monomer synthons. In the processes according to this aspect of the invention, the chemical reactions are stereoretentive so that the products of each reaction retain the same stereoconfiguration as their precursor reagent.

In a third aspect, the invention provides processes for synthesizing oligonucleotides using the well known phosphoramidite approach. In the processes according to this aspect of the invention, any of the monomer synthons according to the invention is used in place of the conventional beta-cyanoethyl phosphoramidite.

20 Claims, No Drawings

OTHER PUBLICATIONS

Zurita et al., *Proc. Natl. Acad. Sci.*, 2340 (1987).
Stahl and Prusiner, *FASEB J.*, 5, 2799 (1991).
Sum et al., J. Am. Chem. Soc. Perkin Trans. I, p. 3183 (1994).
Cary et al., *J. Am. Chem. Soc. Perkin Trans I*, p. 831 (1993).
Beaucage and Iyer, *Tetrahedron Lett.*, 48 2223 (1992).
Bentrude et al., *J. Am. Chem. Soc.*, 111 3981 (1989).
Iyer et al., *Bioorg. Med. Chem. Lett.* 4, 2471 (1994).
Agrawal and Sarin, *Advanced Drug Delivery Rev.*, 6, 251 (1991).
Beaucage, *Methods In Molecular Biology*, 20, 33–61 (1993).
Khorana et al., *J. Molec. Biol.*, 72, 209 (1972).
Reese, *Tetrahedron Lett.*, 34, 3143–3179 (1978).
Beaucage et al., *Tetrahedron Lett.*, 22, 1859–1862 (1981).
Agrawal et al., *Tetrahedron Lett.*, 28, 3539–3542 (1987).
Connolly et al., *Biochemistry*, 23, 3443 (1984).
Jager et al., *Biochemistry*, 27, 7237 (1988).
Agrawal et al., *Proc. Antl. Acad. Sci.* 85, 7079–7083 (1988).
Padmapriya et al., *Antisense Res. Dev.*, 4, 185 (1994).
Ravikumar et al., *Tetrahedron*, 50, 9255 (1994).
Theisen et al., *Nucleosides & Nucleotides*, 12, 43 (1994).
Iyer et al., *Nucleosides & Nucleosides*, 14, 1349 (1995).
Kuijpers et al., *Nucl. Acids Res.*, 18, 5197 (1990).
Reddy et al., *Tetrahedron Lett.*, 35, 4311 (1994).
Tang et al., *Nucleosides & Nucleosides*, 14, 958 (1995).
Koziolkiewicz et al., J. Antisense Nucl. Acid Drug Dev., 7, 43 (1997).
Wang et al., *Tetrahedron Lett.*, 38, 3797 (1997).
Iyer et al., *J. Org. Chem.* 60, 5388 (1995).
Iyer et al., *J. Org. Chem.*, 55, 4693 (1990).
Zon, *Methods In Molecular Biology*, vol. 20, pp. 465 (1993).
Agrawal and Iyer, *Curr. Op. In Biotech*, 6, 12 (1995).
Zon and Stec, *Oligonucleotides and Analogues: A Practical Approach*, pp. 87–108 (1991).

SYNTHONS FOR OLIGONUCLEOTIDE SYNTHESIS

This is a continuation-in-part of U.S. application Ser. No. 08/457,198, filed Jun. 1, 1995 (abandoned), U.S. application Ser. No. 08/597,434, filed Feb. 8, 1996 (abandoned), and U.S. application Ser. No. 08/448,131, filed May 23, 1995 now U.S. Pat. No. 5,750,674.

BACKGROUND OF THE INVENTION

1. Field of the Invention

The invention relates to the chemical synthesis of oligonucleotides and to chemical entities useful in such synthesis.

2. Summary of the Related Art

Oligonucleotides have become indispensable tools in modern molecular biology, being used in a wide variety of techniques, ranging from diagnostic probing methods to PCR to antisense inhibition of gene expression. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See e.g., *Methods in Molecular Biology, Vol 20: Protocols for Oligonucleotides and Analogs* pp. 165–189 (S. Agrawal, Ed., Humana Press, 1993); *Oligonucleotides and Analogues: A Practical Approach*, pp. 87–108 (F. Eckstein, Ed., 1991); and Ulhinann and Peyman, supra. Agrawal and Iyer, *Curr. Op. in Biotech.* 6, 12 (1995); and *Antisense Research and Applications* (Crooke and Lebleu, Eds., CRC Press, Boca Raton, 1993). Early synthetic approaches included phosphodiester and phosphotriester chemistries. Khorana et al., *J. Molec. Biol.* 72, 209 (1972) discloses phosphodiester chemistry for oligonucleotide synthesis. Reese, *Tetrahedron Lett.* 34, 3143–3179 (1978), discloses phosphotriester chemistry for synthesis of oligonucleotides and polynucleotides. These early approaches have largely given way to the more efficient phosphoramidite and H-phosphonate approaches to synthesis. Beaucage and Caruthers, *Tetrahedron Lett.* 22, 1859–1862 (1981), discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

Both of these modern approaches have been used to synthesize oligonucleotides having a variety of modified internucleotide linkages. Agrawal and Goodchild, *Tetrahedron Lett.* 28, 3539–3542 (1987), teaches synthesis of oligonucleotide methylphosphonates using phosphoramidite chemistry. Connolly et al., *Biochemistry* 23, 3443 (1984), discloses synthesis of oligonucleotide phosphorothioates using phosphoramnidite chemistry. Jager et al., *Biochemistry* 27, 7237 (1988), discloses synthesis of oligonucleotide phosphoramidates using phosphoramidite chemistry. Agrawal et al., *Proc. Antl. Acad. Sci. USA* 85, 7079–7083 (1988), discloses synthesis of oligonucleotide phosphoramidates and phosphorothioates using H-phosphonate chemistry.

Solid phase synthesis of oligonucleotides by each of the foregoing methods involves the same generalized protocol. Briefly, this approach comprises anchoring the 3'-most nucleoside to a solid support functionalized with amino and/or hydroxyl moieties and subsequently adding the additional nucleosides in stepwise fashion. Desired internucleoside linkages are formed between the 3' functional group of the incoming nucleoside and the 5' hydroxyl group of the 5'-most nucleoside of the nascent, support-bound oligonucleotide.

Refinement of methodologies is still required, however, particularly when making a transition to large-scale synthesis (10 μmol to 1 mmol and higher). See Padmapriya et al., *Antisense Res. Dev.* 4, 185 (1994). Several modifications of the standard phosphoramidite methods have already been reported to facilitate the synthesis (Padmapriya et al., supra; Ravikamar et al., *Tetrahedron* 50, 9255 (1994); Theisen et al., *Nucleosides & Nucleotides* 12, 43 (1994); and Iyer et al., *Nucleosides & Nucleotides* 14, 1349 (1995)) and isolation (Kuijpers et al. *Nucl. Acids Res.* 18, 5197 (1990); and Reddy et al., *Tetrahedron Lett.* 35, 4311 (1994)) of oligonucleotides.

There has been recent interest in stereodefined phosphorothioate antisense oligonucleotides. Recently, enzymatic synthesis of "all [$R_p$]" PS-oligos was achieved using nucleoside 5'-[$S_p$]-α-thiotriphosphates in conjunction with DNA polymerase. Tang et al., *Nucleosides Nucleotides* 14, 985 (1995). But enzymatic methodology is not as yet amenable to large-scale work, and in addition, does not provide [$S_p$] PS-oligos.

Attempts to achieve stereoselective synthesis of PS-oligonucleotides using phosphoramidite chemistry in conjunction with diastereomerically pure phosphoramidites has not been successful. Thus, when pure [$R_p$] or [$S_p$] nucleoside β-cyanoethyl phosphoramidites were employed in the synthesis of PS-oligos, a mixture of [$R_p$] and [$S_p$] PS-oglios were produced. For a review, see: Beaucage and Iyer, *Tetrahedron* 48, 2223 (1992). Presumably, this was because of the 1H-tetrazole-mediated epimerization of the phosphorous center during the coupling step of oligonucleotide synthesis. Nucleoside oxathiaphospholane is a novel synthon developed by Stec and coworkers to prepare short, but stereodefined PS-oligos. Koziolkiewicz et al., *J. Antisense Nucl. Acid Drug. Dev.* 7, 43 (1997) and references therein. However, this approach requires: (a) prior separation on the individual P-diastereomers (b) need longer coupling reactions compared to standard phosphoramidite chemistry, and (c) the presence of unprotected phosphorothioate functionality generated during the coupling reaction may potentially cause the formation of side products during oligonucleotide synthesis. An interesting stereoselective route towards TpsT using indoloxazaphosphorine intermediate was disclosed recently. Wang and Just, *Tetrahedron Lett* 38, 3797 (1997) and references therein.

Iyer et al., *J. Org. Chem.* 60, 5388 (1995) reported the use of oxazaphospholidines as alternate synthons in oligonucleotide synthesis. Iyer et al., *Tetrahedron Asymmetry* 6, 1051 (1995) reported the stereoselective synthesis of dinucleoside phosphorothioates using a related oxazaphospholidine. The increased reactivity of the P(III) center towards nucleophilic attack and the conformational restraint imposed by the 5-membered ring in the oxazaphospholidine was expected to out-compete the tetrazole-catalyzed epimerization at the P-stereocenter during coupling. Additionally, the presence of the chiral auxiliary in the ring could provide the requisite facial bias in the nucleophilic attack by the support-bound nucleoside on the oxazaphospholidine.

BRIEF SUMMARY OF THE INVENTION

The invention provides new reagents and processes for synthesizing oligonucleotides, including stereoselective oligonucleotide synthesis.

In a first aspect, the invention provides novel monomer synthons for the synthesis of oligonucleotides. Novel monomer synthons according to the invention are characterized by the general structure I:

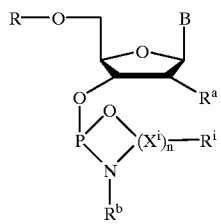

I wherein

R$^a$ and R$^b$, and each R$^i$ are independently H or a C$_1$–C$_{20}$ alkyl, aryl, heterocyclyl, alkoxyalkoxy, or alkoxy group, R is a suitable protecting group (see Sonveaux in *Methods in Molecular Biology, Vol. 26: Protocols for Oligonucleotide Conjugates* (Agrawal, Ed., Human Press, 1994), n is 1, 2 or 3, i is from 1 to n, X$^i$ is CH, O, S, or N, provided that if n is 3 then (a) X$^2$ is optionally O, S or N, (b) X$^1$ and X$^3$ are CH, and (c) there is no R$^2$ when X$^2$ is O or S, and when n>1 the identity of each X$^i$ (i.e., each of X$^1$ . . . X$^n$) is independent of the identity of every other X$^i$ and the identity of each substituent R$^i$ (i.e., each of R$^1$ . . . R$^n$) is independent of every other R$^i$, each R$^i$ is covalently bound to the corresponding X$^i$ (e.g., X$^1$–R$^1$ . . . X$^n$–R$^n$), the X$^i$ are arranged consecutively such that X$^1$ is bound to the N and X$^n$ is bound to the O to form an n+3 membered ring, each chiral X$^i$ is predominantly in a single stereoconfiguration, R$^b$, the N to which it is bonded, X$^1$ and R$^1$ optionally form a five-membered heterocyclic ring, and B is any suitably protected modified or unmodified purine or pyrimidine base.

In one preferred embodiment of a monomer synthon according to this aspect of the invention, R$^a$ is H, n is 2 and X$^1$ and X$^2$ are each C. In a particularly preferred embodiment of a monomer synthon according to this aspect of the invention, n is 2, X$^1$ and X$^2$ are each CH, R$^1$ is methyl, R$^2$ is phenyl, R$^a$ is H, R$^b$ is methyl, and the synthon has the R$_p$ configuration. In another particularly preferred embodiment of a monomer synthon according to this aspect of the invention, n is 2, X$^1$ and X$^2$ are each CH, R$^1$ and R$^2$ are each H, R$^a$ is H, and R$^b$ is methyl.

In another embodiment of compound I, a monomer synthon comprising a bicyclic oxazaphospholidine of formula L is provided:

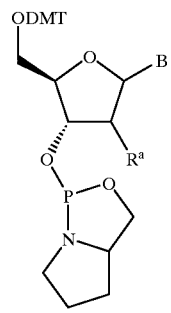

L

In a preferred embodiment of L, R$^a$ is H or methoxy.

Certain preferred monomer synthons according to this aspect of the invention are pentavalent at the phosphorous atom. These preferred monomer synthons are characterized by the general structure V:

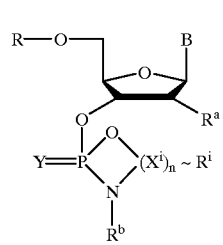

V wherein

Y is sulfur or an isotope of oxygen,

R$^a$ and R$^b$, and each R$^i$ are independently H or a C$_1$–C$_{20}$ alkyl, aryl, heterocyclyl, alkoxyalkoxy, or alkoxy group, R is a suitable protecting group, n is 1, 2 or 3, i is 1–n, X$^1$ is CH, O, S, or N, provided that if n is 3 then (a) X$^2$ is optionally O, S or N, (b) X$^1$ and X$^3$ are CH, and (c) there is no R$^2$ when X$^2$ is O or S, and when n>1 the identity of each X$^i$ (i.e., each of X$^1$ . . . X$^n$) is independent of the identity of every other X$^i$ and the identity of each substituent R$^i$ (i.e., each of R$^1$ . . . R$^n$) is independent of every other R$^i$, each R$^i$ is covalently bound to the corresponding X$^i$ (e.g., X$^1$–R$^1$ . . . X$^n$–R$^n$) the X$^i$ are arranged consecutively such that X$^1$ is bound to the N and X$^n$ is bound to the O to form an n+3 membered ring, each chiral X$^i$ is predominantly in a single stereoconfiguration, R$^b$, the N to which it is bonded, X$^1$ and R$^1$ optionally form a five-membered heterocyclic ring, and B is any suitably protected modified or unmodified purine or pyrimidine base.

In one preferred embodiment of a monomer synthon according to the general structure V, R$^a$ is H, n is 2 and X$^1$ and X$^2$ are each C. In a particularly preferred embodiment of a monomer synthon according to this structure, n is 2, X$^1$ and X$^2$ are each CH, R$^1$ is methyl, R$^2$ is phenyl, R$^a$ is H, R$^b$ is methyl, and the synthon may be the anti-isomer or the syn-isomer. In another particularly preferred embodiment of a monomer synthon according to structure VI, n is 2, $X^1$ and $X^2$ are each CH, $R^1$ and $R^2$ are each H, $R^a$ is H, and $R^b$ is methyl. In another preferred embodiment, $R^b$, the N to which it is bonded, $X^1$ and $R^1$ form a five-membered heterocyclic ring.

Monomer synthons according to this aspect of the invention are useful in the synthesis of oligonucleotides and can be used in place of the well known beta-cyanoethyl phosphoramidite monomer synthon in the phosphoramidite synthesis procedure. Certain monomer synthons according to this aspect of the invention are useful in this procedure for producing oligonucleotides having defined stereochemistry.

In a second aspect, the invention provides processes for synthesizing monomer synthons according to the invention, including diastereomerically enriched or purified monomer synthons. In the processes according to this aspect of the invention, the chemical reactions are stereoretentive so that the products of each reaction retain the same stereoconfiguration as their precursor reagent. In the most general process according to this aspect of the invention, the reagent $PCl_3$ is reacted with a compound having the structure X:

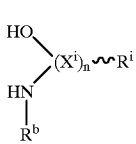

X wherein $R^b$ and each $R^i$ are independently H or a $C_1$–$C_{20}$ alkyl, aryl, heterocyclyl, alkoxyalkoxy or alkoxy group, n is 1, 2, or 3, i is 1 to n, $X^i$ is CH, O, S, or N, provided that if n is 3 then (a) $X^2$ is optionally O, S or N, (b) $X^1$ and $X^3$ are CH, and (c) there is no $R^2$ when $X^2$ is O or S, and when n>1 the identity of each $X^i$ (i.e., each of $X^1 \ldots X^n$) is independent of the identity of every other $X^i$ and the identity of each substituent $R^i$ (i.e., each of $R^1 \ldots R^n$) is independent of every other $R^i$, each $R^i$ is covalently bound to the corresponding $X^i$ (eg., $X^1$–$R^1 \ldots X^1$–$R^1$), the $X^i$ are arranged consecutively such that $X^1$ is bound to the N and $X^n$ is bound to the O to form an n+3 membered ring, each chiral $X^i$ is predominantly in a single stereoconfiguration, $R^b$, the N to which it is bonded, $X^1$ and $R^1$ optionally form a five-membered heterocyclic ring, to yield the structure XI:

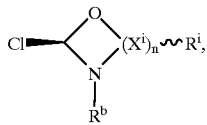

XI which is then reacted with a nucleoside having a protected 5' hydroxyl and unprotected 3' hydroxyl to yield the previously described monomer synthon structure I. In a preferred embodiment of this process according to the invention, in the compound having the structure X, n is 2 and $X^1$ and $X^2$ are each C. In a particularly preferred embodiment of the process according to this aspect of the invention, the process comprises the step of reacting a pure stereoisomer of ephedrine with $PCl_3$. When the stereoisomer (1R, 2S)-(−)-ephedrine is used, the result is a yield of about 75% of a chlorophosphoramidite product which is 95% in the $R_p$ isomer configuration. This compound reacts with a nucleoside having a protected 5' hydroxyl and unprotected 3' hydroxyl to yield a stereoregular monomer synthon. The other stereoisomers of ephedrine (1S,2R; 1S,2S; and 1R,2R) can be used in place of (1R,2S)-(−)-ephedrine to obtain their corresponding stereoregular monomer synthons. In another preferred embodiment of the process according to this aspect of the invention, in the compound having structure X, $X^1$ and $X^2$ are each CH, $R^1$ and $R^2$ are each H, and $R^b$ is $CH_3$. In yet another preferred embodiment, $R^b$, the N to which it is bonded, $X^1$ and $R^1$ form a five-membered heterocyclic ring.

In another preferred embodiment of a process according to this aspect of the invention, the previously described monomer synthons having structure I, or the previously described particularly preferred embodiments thereof, are oxidized stereoretentively to yield respectively the previously described monomer synthon structure V, or the previously described particularly preferred embodiments thereof.

In another preferred embodiment, the process according to this aspect of the invention can be used to provide both the anti- and syn- isomer synthons for stereoselective oligonucleotide synthesis. The isomers are then readily separated by conventional chromatography or crystallization. In another preferred embodiment, the process according to this aspect of the invention can be used to produce a new monomer synthon for non-stereoselective synthesis of phosphorothioate or phosphodiester oligonucleotides.

In any of the above preferred embodiments of the process according to this aspect of the invention, the oxidation can be an oxidative thiolation of the phosphorous, and the constituent Y of the compound V thereby produced is sulfur. Alternatively, the oxidation can be an oxygenation of the phosphorous, and the constituent Y of the compound V thereby produced is oxygen, most preferably an isotope of oxygen other than $^{18}O$.

In a third aspect, the invention provides processes for synthesizing oligonucleotides using the well known phosphoramidite approach. In the processes according to this aspect of the invention, any of the monomer synthons according to the invention is used in place of the conventional beta-cyanoethyl phosphoramidite.

In one preferred embodiment, synthon I, or one of the particularly preferred embodiments is used in the synthesis process. The synthon is contacted in the presence of a suitable activating agent, such as tetrazole, with a nascent oligonucleotide (including a support-bound mononucleoside) having a free 5' hydroxyl to form a phosphite internucleoside linkage. The phosphite internucleoside linkage is then oxidized using a suitable oxidizing agent. When a chiral preferred embodiment of synthon I is used in the synthesis process, the resulting oligonucleotides generally have predominantly $S_p$ configuration at each internucleoside linkage at which such chiral synthon was used during synthesis.

In another preferred embodiment, synthon V or one of its particularly preferred embodiments is used in the synthesis process. The synthon is contacted in the presence of a suitable activating agent, such as tetrazole, with a nascent oligonucleotide (including a support-bound mononucleoside) having a free 5' hydroxyl. In this case, the synthon has already been oxidized at the phosphorous atom, so the resulting internucleoside linkage is a phosphodiester or phosphorothioate linkage. When a chiral preferred embodiment of synthon V is used and constituent Y is sulfur or an isotope of oxygen other than $^{18}O$, the resulting oligonucleotide has a $R_p:S_p$ ratio of about 70:30 or 10:90, depending on which epimer of V is used.

The process according to this aspect of the invention utilizes phosphoramidite chemistry for any cycles in which any of the monomer synthons according to the invention are used. However, in other cycles, the process according to this aspect of the invention can utilize any suitable oligonucleotide synthesis chemistry, including the well known H-phosphonate, phosphotriester and phosphoramidite chemistries.

DETAILED DESCRIPTION OF THE PREFERRED EMBODIMENTS

The invention relates to the chemical synthesis of oligonucleotides and to chemical entities useful in such synthesis. The patents and publications identified in this specification are within the knowledge of those skilled in this field and are hereby incorporated by reference in their entirety.

The invention provides new reagents and processes for synthesizing oligonucleotides, including stereoselective oligonucleotide synthesis.

In a first aspect, the invention provides novel monomer synthons for the synthesis of oligonucleotides. Novel monomer synthons according to the invention are characterized by the general structure I:

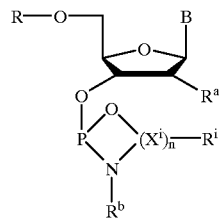

I wherein $R^a$ and $R^b$, and each $R^i$ are independently H or a $C_1$–$C_{20}$ alkyl, aryl, heterocyclyl, alkoxyalkoxy or alkoxy group, R is a suitable protecting group (see Sonveaux in *Methods in Molecular Biology, Vol. 26: Protocols for Oligonucleotide Conjugates* (Agrawal, Ed., Humana Press Inc., Totowa, N.J. 1994), n is 1, 2, or 3, i is from 1 to n, $X^i$ is CH, O, S, or N, provided that if n is 3 then (a) $X^2$ is optionally O, S or N, (b) $X^1$ and $X^3$ are CH, and (c) there is no $R^2$ when $X^2$ is O or S, and when n>1 the identity of each $X^i$ (i.e., each of $X^1$ ... $X^n$) is independent of the identity of every other $X^i$ and the identity of each substituent $R^i$ (i.e., each of $R^1$ ... $R^n$) is independent of every other $R^i$, each $R^i$ is covalently bound to the corresponding $X^i$ (e.g., $X^1$–$R^1$ ... $X^n$–$R^n$), the $X^i$ are arranged consecutively such that $X^1$ is bound to the N and $X^n$ is bound to the O to form an n+3 membered ring, each chiral $X^i$ is predominantly in a single stereoconfiguration, $R^b$, the N to which it is bonded, $X^1$ and $R^1$ optionally form a five-membered heterocyclic ring, and B is any suitably protected modified or unmodified purine or pyrimidine base (see Sonveaux, supra and Meyer, *Methods in Molecular Biology*, Vol. 26, pp. 73–92).

To further clarify the nature of general structure I, general structure Ia is a sub-genus of structure I wherein n=2, and general structure Ib is a sub-genus of structure I wherein n=3:

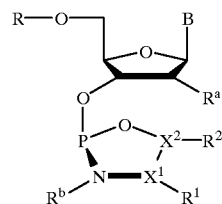

Ia

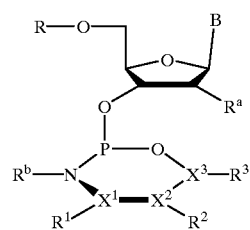

Ib

As used throughout this disclosure, the term "aryl" means a polyaromatic ring structure having from 1 to 5 linearly or angularly fused aromatic rings, such as phenyl and naphthyl. As used throughout this disclosure, the terms "heterocyclic" and "heterocyclyl" mean a 5 or 6 membered ring having from 1 to 5 heteroatoms (i.e., N, S, or O) which may be located at any position within the ring, examples of which include furan and thiophene. An "alkoxy" moiety has the stucture $CH_3(CH_2)_dO$— where d is from 0 to 5.

In one preferred embodiment of a monomer synthon according to this aspect of the invention, $R^a$ is H, n is 2 and $X^1$ and $X^2$ are each CH, resulting in the structure II:

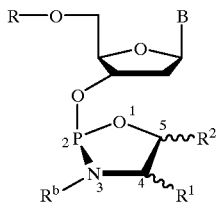

II

In this preferred embodiment, the configurations at carbons 4 and 5 can be, respectively, R and S, S and R, R and R, or S and S, each of which can be obtained in pure form.

In a particularly preferred embodiment of a monomer synthon according to this aspect of the invention, n is 2, $X^1$ and $X^2$ are each CH, $R^1$ is methyl, $R^2$ is phenyl, $R^a$ is H, $R^b$ is methyl, and the synthon has the $R_p$ configuration shown in structure III:

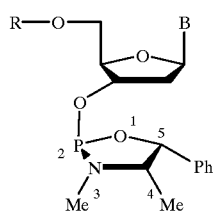

III

In another particularly preferred embodiment of a monomer synthon according to this aspect of the invention, n is 2, $X^1$ and $X^2$ are each CH, $R^1$ and $R^2$ are each H, $R^a$ is H, $R^b$ is methyl, and the synthon is the phosphoramidite synthon shown in structure IV:

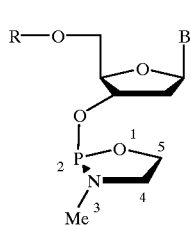

IV

In another preferred embodiment of compound I, n is 2, $R^b$ is $(CH_2)_2$, $X^1$ and $X^2$ are CH, $R^1$ is $CH_2$, $R^2$ is H, and $R^b$, the N to which it is bonded, $X^1$ and $R^1$ form a five-membered heterocyclic ring, which is the bicyclic oxazaphospholidine monomer synthon of formula L:

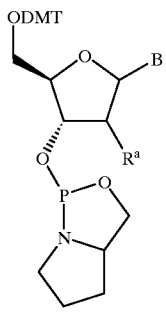

L

In a preferred embodiment of L, $R^a$ is H or methoxy.

Certain preferred monomer synthons according to this aspect of the invention are pentavalent at the phosphorous atom and can be synthesized by oxidation of their counterparts that are trivalent at the phosphorous atom. These preferred monomer synthons are characterized by the general structure V:

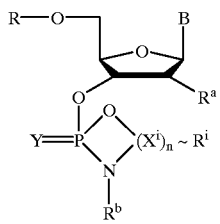

V wherein

Y is sulfur or an isotope of oxygen, $R^a$ and $R^b$, and each $R^i$ are independently H or a $C_1$–$C_{20}$ alkyl, aryl, heterocyclyl, alkoxyalkoxy or alkoxy group, R is a suitable protecting group (see Sonveaux in *Methods in Molecular Biology*, Vol. 26: *Protocols for Oligonucleotide Conjugates* (Agrawal, Ed., Humana Press Inc., Totowa, N.J. 1994), n is 1, 2, or 3, i is from 1 to n, $X^i$ is CH, O, S, or N, provided that if n is 3 then (a) $X^2$ is optionally O, S or N, (b) $X^1$ and $X^3$ are CH, and (c) there is no $R^2$ when $X^2$ is O or S, and when n>1 the identity of each $X^1$ (i.e., each of $X^1$ . . . $X^n$) is independent of the identity of every other $X^i$ and the identity of each substituent $R^i$ (i.e., each of $R^1$ . . . $R^n$) is independent of every other $R^i$, each $R^i$ is covalently bound to the corresponding $X^i$ (e.g., $X^1$–$R^1$ . . . $X^n$–$R^n$), the $X^i$ are arranged consecutively such that $X^1$ is bound to the N and $X^n$ is bound to the O to form an n+3 membered ring, each chiral $X^i$ is predominantly in a single stereoconfiguration, $R^b$, the N to which it is bonded, $X^1$ and $R^1$ optionally form a five-membered heterocyclic ring, and B is any suitably protected modified or unmodified purine or pyrimidine base (see Sonveaux, supra and Meyer, *Methods in Molecular Biology*, Vol. 26, pp. 73–92).

In one preferred embodiment of a monomer synthon according to the general structure V, $R^a$ is H, n is 2 and $X^1$ and $X^2$ are each CH, resulting in the structure VI:

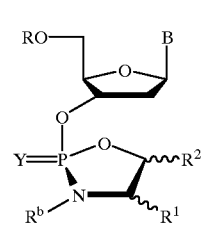

VI

In a particularly preferred embodiment of a monomer synthon according to structure VI, n is 2, $X^1$ and $X^2$ are each CH, $R^1$ is methyl, $R^2$ is phenyl, $R^a$ is H, $R^b$ is methyl, and the synthon may be the anti-isomer shown in structure VII or the syn-isomer shown in structure VIII:

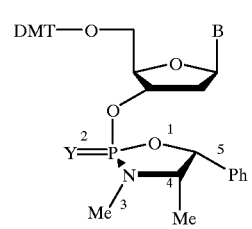

VII

-continued

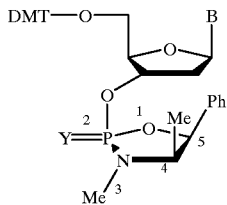

VIII

In another particularly preferred embodiment of a monomer synthon according to structure VI, n is 2, $X^1$ and $X^2$ are each CH, $R^1$ and $R^2$ are each H, $R^a$ is H, $R^b$ is methyl, and the synthon is the phosphoramidite synthon shown in structure IX:

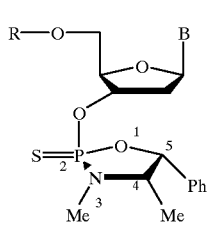

IX

In another preferred embodiment of V, n is 2, $R^b$ is $(CH_2)_2$, $X^1$ and $X^2$ are CH, $R^1$ is $CH_2$, $R^2$ is H, and $R^b$, the N to which it is bonded, $X^1$ and $R^1$ form a five-membered heterocyclic ring:

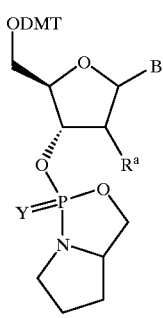

LV

Particularly preferred is compound LV wherein Y is S and $R^a$ is H or methoxy.

Monomer synthons according to this aspect of the invention are useful in the synthesis of oligonucleotides and can be used in place of the well known beta-cyanoethyl phosphoramidite monomer synthon in the phosphoramidite synthesis procedure (see e.g., Beaucage in *Methods in Molecular Biology*, Vol. 20, *Protocols for Oligonucleotides and Analogs*, pp. 33–61). Certain synthons having the structures I–III, L, V–VIII, and LV are useful in this procedure for producing oligonucleotides having defined stereochemistry.

In a second aspect, the invention provides processes for synthesizing monomer synthons according to the invention, including diastereomerically enriched or purified monomer synthons. In the processes according to this aspect of the invention, the chemical reactions are stereospecific so that the products of each reaction possess a defined stereoconfiguration. In the most general process according to this aspect of the invention, the reagent $PCl_3$ is reacted with a compound having the structure X:

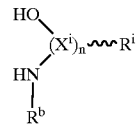

X wherein
$R^b$ and each $R^i$ are independently H or a $C_1$–$C_{20}$ alkyl, aryl, heterocyclyl, alkoxyalkoxy or alkoxy group,
n is 1, 2, or 3,
i is from 1 to n,
$X^i$ is CH, O, S, or N, provided that if n is 3 then (a) $X^2$ is optionally O, S or N, (b) $X^1$ and $X^3$ are CH, and (c) there is no $R^2$ when $X^2$ is O or S, and when n>1 the identity of each $X^i$ (i.e., each of $X^1$ . . . $X^n$) is independent of the identity of every other $X^i$ and the identity of each substituent $R^i$ (i.e., each of $R^1$ . . . $R^n$) is independent of every other $R^i$, each $R^i$ is covalently bound to the corresponding $X^i$ (e.g., $X^1$–$R^1$ . . . $X^n$–$R^n$), the $X^i$ are arranged consecutively such that $X^1$ is bound to the N and $X^n$ is bound to the O to form an n+3 membered ring, each chiral $X^i$ is predominantly in a single stereoconfiguration, and
$R^b$, the N to which it is bonded, $X^1$ and $R^1$ optionally form a five-membered heterocyclic ring, to yield the structure XI:

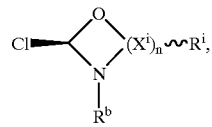

XI which is then reacted with a nucleoside having a protected 5' hydroxyl and unprotected 3' hydroxyl to yield the previously described monomer synthon structure I.

In a preferred embodiment of this process according to the invention, in the compound having the structure X, n is 2 and $X^1$ and $X^2$ are each CH, resulting in the structure XII,

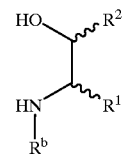

XII which, when reacted with $PCl_3$, produces the structure XIII:

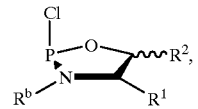

XIII which is then reacted with a nucleoside having a protected 5' hydroxyl and unprotected 3' hydroxyl to yield the previously described monomer synthon structure II.

In a particularly preferred embodiment of the process according to this aspect of the invention, the process comprises the step of reacting a pure stereoisomer of ephedrine with PCl₃, preferably at a temperature between minus 100 and +40° C. for a time between one and 40 hours, most preferably in N-methyl morpholine and toluene at −78° C. for three hours and then 22° C. for 12 hours. Other suitable solvents are benzene, tetrahydrofuran, ether and dioxane.

When the stereoisomer (1R, 2S)-(−)-ephedrine is used, the result is a yield of about 75% of a chlorophosphoramidite product having the structure XIV, which is 95% in the $R_p$ isomer configuration:

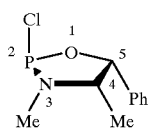

XIV

This compound is fairly stable, undergoing no decomposition detectable by ³¹P-NM after being stored at −5° C. for several days. It reacts with a nucleoside having a protected 5' hydroxyl and unprotected 3' hydroxyl to yield the previously described monomer synthon structure III in high yield (84%). Most preferably, the reaction with the nucleoside is carried out in the presence of a scavenger of the HCl liberated during the reaction, such as triethylamine, pyridine, and 2,6-lutidine. The other stereoisomers of ephedrine (1 S,2R; 1 S,2S; and 1R,2R) are also commercially available and can be used in place of (1R,2S)-(−)-ephedrine to obtain, respectively, compounds having structures XV, XVI, and XVII:

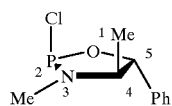

XV

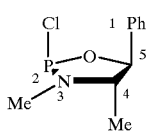

XVI

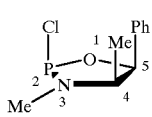

XVII any of which reacts with a nucleoside having a protected 5' hydroxyl and unprotected 3' hydroxyl to yield the corresponding other stereoisomer of the previously described monomer synthon structure III.

In another particularly preferred embodiment of the process according to this aspect of the invention, the process comprises the step of reacting a compound having the structure XVIII (i.e., compound X wherein n is 2, $X^1$ and $X^2$ are CH, $R^b$ is CH₃, and $R^1$ and $R^2$ are H):

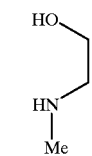

XVIII with PCl₃ to yield a compound having the structure XIX:

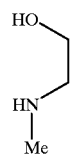

XIX which reacts with a nucleoside having a protected 5' hydroxyl and unprotected 3' hydroxyl to yield the previously described monomer synthon structure IV.

In another embodiment of this aspect of the invention, a process is provided for the synthesis of monomer synthon L, comprising reacting (S)-pyrrolidin-2-ylmethanol (which is a compound of formula X wherein n is 2, $R^b$ is (CH₂)ₙ, $X^1$ and $X^2$ are CH, $R^1$ is CH₂ and $R^2$ is H and $R^b$, the N to which it is bonded, $X^1$ and $R^1$ form a five-membered heterocyclic ring, pyrrolidinyl):

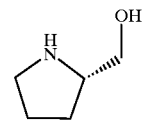

with PCl₃ (e.g., in triethylamine) to yield the P-chloro-oxazaphospholidine LI:

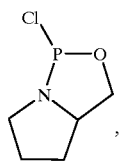

LI which is then reacted with a 5'-dimethoxytrityl nucleoside

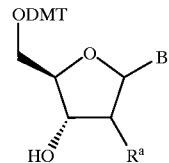

(e.g., in disopropylethylamine) to yield the monomer synthon L with $S_p$:$R_p$ about 9:1. Similarly, starting with (R)(+)-pyrrolidin-2-ylmethanol yields the monomer synthon L with $S_p$:$R_p$ about 1:9.

In another preferred embodiment of a process according to this aspect of the invention, monomer synthons having the previously described structure I or II are oxidized stereoretentively to yield respectively the previously described monomer synthon structure V or VI. Stereospecific oxidation of a particular stereoisomer of compound I or II results in the oxidation product in approximately 90% yield.

In another preferred embodiment, the process according to this aspect of the invention can be used to provide the anti- isomer synthon previously described as structure VII. In this embodiment, the previously described synthon III is oxidized to yield a mixture containing 90% anti- isomer VII and 10% syn- isomer VIII. Synthons VII and VIII are then readily separated by conventional chromatography or crystallization.

In another preferred embodiment, the process according to this aspect of the invention can be used to provide the synthon previously described as structure IX. In this embodiment, the previously described synthon IV is oxidized to yield the synthon IX.

In any of the above preferred embodiments of the process according to this aspect of the invention, the oxidation can be an oxidative thiolation of the phosphorous, and the constituent Y of the compound V-IX and LV thereby produced is sulfur. Such thiolation may be carried out using any suitable thiolating agent, such as elemental sulfur. (See Stec et al., J. Am. Chem. Soc. 106: 6077 (1984).) Preferably, such oxidative thiolation is carried out using Beaucage reagent, 3H-1,2-benzodithiol-3-one-1,1-dioxide. (See Iyer et al., J. Am. Chem. Soc. 112: 1253 (1990) and Iyer et al., J. Org. Chem. 55: 4693 (1990).) In a most preferred embodiment, Beaucage reagent is used as a 2% solution in acetonitrile and is allowed to react for about thirty seconds at about room temperature with any of compounds I–IV and L. Alternatively, the oxidation can be an oxygenation of the phosphorous, and the constituent Y of the compound V–IX and LV thereby produced is oxygen, most preferably an isotope of oxygen other than $^{18}O$. In this embodiment, the oxidation is carried out using a suitable oxidizing agent in the presence of water, preferably in the presence of water having an isotope of oxygen other than $^{18}O$, such as $^{17}O$. Suitable oxidizing agents include, without limitation, $I_2$, tert-BuOOH and $N_2O_4$ (see Beaucage and Iyer, Tetrahedron 48: 2223 (1992)). Other chiral constituents include, without limitation, selenium and tellurium.

In a third aspect, the invention provides processes for synthesizing oligonucleotides using the well known phosphoramidite approach. (See Beaucage in *Methods in Molecular Biology*, Vol. 20, *Protocols for Oligonucleotides and Analogs*, supra, at pp. 33–61.) In the processes according to this aspect of the invention, any of synthons I–IX and L is used in place of the conventional beta-cyanoethyl phosphoramidite.

In one preferred embodiment, any of synthons I–IV and L are used in the synthesis process. The synthon is contacted in the presence of a suitable activating agent with a nascent oligonucleotide (including a support-bound mononucleoside) having a free 5' hydroxyl to form a phosphite internucleoside linkage. Suitable activating agents include, without limitation, tetrazole, anilinium trifluoroacetate, substituted tetrazole derivatives (e.g., phenyl or thioethyltetrazole) and N,N-dimethylaniline hydrochloride (see Beaucage and Iyer, supra). The phosphite internucleoside linkage is then oxidized using a suitable oxidizing agent. For example, it may be oxidized using $I_2$ and $H_2O$ in THF to yield a phosphodiester internucleoside linkage. If $H_2O$ containing an isotope of oxygen other than $^{18}O$ is used, the phosphodiester internucleoside linkage will be isotopically labeled. Alternatively, the phosphite internucleoside linkage may be oxidized using a thiolating agent, such as $S_8$ or Beaucage reagent, to yield a phosphorothioate internucleoside linkage. When compound III is used in the synthesis process, the resulting phosphorothioate oligonucleotides or isotopically labeled phosphodiester oligonucleotides have predominantly $S_p$ configuration (about 60%) at each internucleoside linkage at which compound III was used during synthesis.

In another preferred embodiment, any of synthons V–IX and LV are used in the synthesis process. The synthon is contacted in the presence of a suitable activating agent with a nascent oligonucleotide (including a support-bound mononucleoside) having a free 5' hydroxyl. Suitable activating agents include, without limitation, hindered non-nucleophilic bases, such as 1,4-diazabicycloundecene, potassium tert-butoxide and t-butyl magnesium chloride. In this case, the synthon has already been oxidized at the phosphorous atom, so the resulting internucleoside linkage is a phosphodiester or phosphorothioate linkage. When compound VII is used and constituent Y is sulfur or an isotope of oxygen other than $^{18}O$, the resulting oligonucleotide has a $R_p$:$S_p$ ratio of about 70:30. When compound VIII is used, the resulting oligonucleotide has a $R_p$:$S_p$ ratio of 10:90. Similar results are obtained using compound V, when constituent Y is sulfur or an isotope of oxygen other than $^{18}O$ and all of the $R^i$ are anti- or syn- with respect to the nucleoside, or using compound VI, when constituent Y is sulfur or an isotope of oxygen other than $^{18}O$ and $R^1$ and $R^2$ are both anti- or both syn- with respect to the nucleoside.

In another embodiment of this aspect of the invention, the monomer synthon L is employed in the synthesis process. The synthon is contacted in the presence of a suitable activating agent (e.g., 1H-tetrazole, as displayed below) with a nascent oligonucleotide (including a support-bound mononucleoside) having a free 5' hydroxyl to yield the corresponding phosphite:

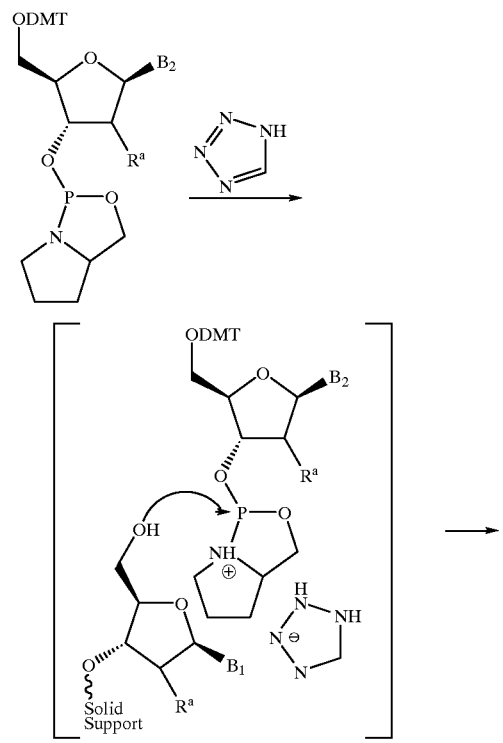

-continued

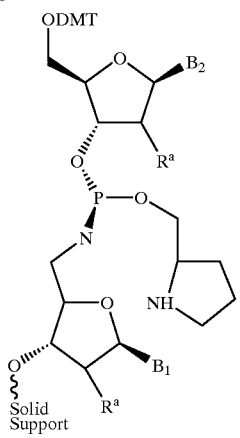

wherein $B_1$ and $B_2$ are the same or different suitably protected modified or unmodified purine or pyrimidine base, and the identity of each $R^a$ is independent of the identity of the others. The phosphate can then be oxidized according to well known methods, as described hereinabove, to yield the corresponding phosphodiester or phosphorothioate:

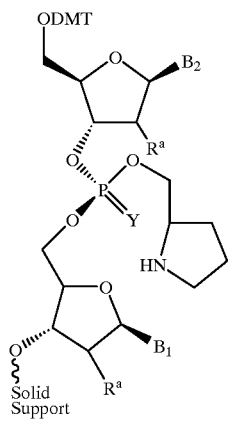

where Y is sulfur or an isotope of oxygen other than $^{18}O$. $S_p:R_p$ are about 9:1 and the coupling efficiency generally greater than 97%. The pyrrolidin-2-ylmethoxy residue can be then be removed by treatment with concentrated ammonia, which may be conducted after an entire oligonucleotide chain has been synthesized.

The process according to this aspect of the invention utilizes phosphoramidite chemistry for any cycles in which any of compounds I–IX, L, and LV (including, of course, their preferred embodiments) are used. However, in other cycles, the process according to this aspect of the invention can utilize any suitable oligonucleotide synthesis chemistry, including the well known H-phosphonate, phosphotriester and phosphoramidite chemistries. In one preferred embodiment, synthesis is carried out on a suitable solid support. Suitable solid supports include any of the standard solid supports used for solid phase oligonucleotide synthesis, such as controlled-pore glass (CPG). (See, eg., Pon, *Methods in Molec. Biol.* 20, 465 (1993)). Synthesis on such a solid support begins with coupling a nucleoside synthon according to the invention to a nucleoside that is covalently linked the solid support (i.e., linked to a functionality on the solid support, preferably an amino or hydroxyl functionality).

In another aspect of the invention, oligonucleotides having one or more P-chiral centers independently predominantly in the R or S configuration and methods for synthesizing them are provided. In one embodiment of this aspect of the present invention, these oligonucleotides can be synthesized via the well-known phosphoramidate approach (eg., Beaucage in *Methods in Molecular Biology, Vol* 20, *Protocols for Oligonculeotides and Analogs,* supra, pp. 33–61 and references cited therein) using the stereospecific monomer synthons described herein. As used herein, "predominantly" means more than half. Antisense oligonucleotides having one or more P-chiral centers independently predominantly in the R or S stereoconfiguration are useful for all purposes for which antisense oligonucleotides have been reported in the patent and scientific literature to be useful, i.e., for inhibition of nucleic acid expression in vitro (e.g., to study the role of a particular nucleic acid's expression product in biological systems) and in vivo (e.g., as a therapeutic agent). Double stranded nucleic acids comprising antisense oligonucleotides according to this aspect of the invention are also useful as transcription factor decoys.

The versatility of chemical synthetic approach of the method according to the invention makes the method according to the invention suitable for the synthesis of any of a broad class of compounds, all of which are referred to herein as "oligonucleotides". For purposes of the invention, the term oligonucleotide includes polymers of two or more deoxyribonucleotide, or 2'-O-substituted ribonucleotide monomers, or any combination thereof. Such monomers may be coupled to each other by any of the numerous known internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/ or having additional substituents, including without limitation lipophilic groups, intercalating agents, diamines and adamantane. For purposes of the invention the term "2'-O-substituted" means substitution of the 2' position of the pentose moiety with an -O-lower alkyl group containing 1–6 saturated or unsaturated carbon atoms, or with an -O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group(to produce a ribonucleoside), an amino or a halo group, but not with a 2'-H group.

The following examples further illustrate certain preferred embodiments of the invention and are not limiting in nature. Unless otherwise stated, all chemicals recited in the following Examples were obtained from Aldrich of Milwaukee, Wis.

EXAMPLES

Example 1

Stereoselective Synthesis of a Mononucleotide Synthon

The chlorophosphoramidite, (2R,4S,5R)-2-chloro-3,4-dimethyl-5-phenyl-1,3,2-oxazaphospholidine (XIV) was obtained by mixing 8.14 g of 1R,2S-ephedrine and 10.4 ml of N-methyl morpholine in 250 ml of toluene under argon and cooling to −78° C. 4.3 ml of $PCl_3$ in 10 ml of toluene was added over a period of 15 minutes. The mixture was kept at −78° C. for 1 hour and then allowed to warm to room temperature over a period of 16 hours. The insoluble salt precipitate was filtered under argon. The precipitate was washed with 3×25 ml of toluene. The combined washings and filtrate were concentrated in vacuo in a rotary evaporator to remove toluene. Vacuum distillation of the residue gave a colorless liquid boiling at 0.1 mm Hg at 95° C. to give ca. 9 g (80% yield) of the product. This procedure is similar to that described previously. Sun et al., *J. Chem. Soc. Perkin Trans. I*, p. 3183 (1994) and references therein and Carey et al., *J. Chem. Soc. Perkin Tarns. I*, p. 831 (1993).

$^{31}$P-NMR examination of the resulting crude reaction mixture revealed the presence of a predominant isomer (>95%) at δ 169.4 ppm and a minor component (<5%) at δ 161 ppm. Upon vacuum distillation of the reaction mixture (95–97° C. at 0.1 mm Hg), a colorless liquid was obtained, which solidified to a white crystalline mass upon cooling to −78° C. (isolated yields of 75%). Carey et al, supra, reported a b.p. of 160° C. at 0.1 mm Hg. NMR analysis gave the following results: $^{31}$P-NMR (CDCl$_3$) (TMP external standard) δ 169.1 ppm; $^1$H-NMR (CDCl$_3$) δ (ppm) 0.71 (3H, d, J=6.3 Hz), 2.69 (3H, d, $^3J_{P-H}$=15.1 Hz, N-CH$_3$), 3.63 (1H, ddq, J=1.3, 5.5,$^3$JP-H=7.6 Hz, H-4), 5.85 (1H, dd, J=5.5 Hz, $^3J_{P-H}$~11.2 Hz), 7.15 (5H, m, -Ph). These spectral features are in agreement with values reported by Sun et al. and Carey et al., supra, and lead to the assignment of structure XIV as being the R isomer in which the chlorine atom is disposed trans relative to the C-Ph and C-Me substituents in the pholidine ring. XIV could be stored as a solid in a desiccator at −5° C. for several days with no apparent decomposition (as evaluated by $^{31}$P-NMR). Upon addition of water to XIV, the H-phosphonate was obtained as a mixture of diastereomers (R$_p$:S$_p$, 55:45 $^{31}$P-NM).

2.16 g of 5'-O-dimethoxytrityl thymidine was dissolved in a mixture of anhydrous ether (20 ml) and anhydrous triethylamnine (5 ml). The solution was added gradually (10 min) to 1.2 g of the chlorophosphoramidite (XIV) at room temperature and the solution stirred at room temperature for 6 hours. The reaction mixture was poured into 200 ml of ice-cold water. It was then extracted with ethylacetate (3×200 ml). The combined organic layer was washed with water. The organic layer was evaporated to dryness to give 3 g (84% yield) of III as a white foamy material.

Synthesis of I and II is conducted according to the same protocol.

The $^{31}$P-NMR spectrum of III has a signal at δ 140 ppm, corresponding to a single P-epimer. In analogy with substitution reactions of III involving carbon-, oxygen-, and nitrogen-based nucleophiles (Sun et al. and Carey et al., supra), which gave substitution products with overall retention of configuration, VI can be formulated as having the structure with R$_p$ configuration. This hitherto unreported nucleoside phosphoramidite III is a white solid and is stable when stored dry at 0–5° C. The NMR and mass spectral features of III are as follows: $^{31}$P-NMR (CDCl$_3$) (TMP ext. standard) δ 169 ppm; $^1$H-NMR (CDCl$_3$) δ (ppm) 0.61 (3H, d, J=6.5 Hz), 1.41 (3H, s, T-CH)$_3$ 2.42 (2H, m, H-2'), 2.63 (3H, d, $^3J_{P-H}$=12 Hz, N-CH$_3$), 3.37 (1Hm, dd, J=10.6, 2.6 Hz, H-5') 3.46 (1H, dd, J=10.6, 2.6 Hz, H-5'), 3.52 (1H, ddq, J=6.9, 6.5 Hz, $^3J_{P-H}$=2.4 Hz, H-4), 3.76 (6H, s, —OCH$_3$), 4.08 (1H, m, H-4'), 4.91 (1H, m, H-3'), 5.56 (1H, dd, J=6.9 Hz, $^3J_{P-H(5)}$=1.84 Hz, H-5), 6.41 (1H, dd, J=6.7, 6.7 Hz, H-1'), 6.85 (4H, m, —Ph), 7.25 (14H, m, —Ph), -76. (1H, s, H-6), 9.1 (1H, s, —NH). FAB-MS (m/z)=736 (M-H), C$_4$,H$_{44}$N$_3$O$_8$P.

Oxidative sulfurization of the phosphoramidite III with thiolsulfonate (R.I. Chemicals, Costa Mesa, Calif.) according to Iyer et al., *J. Am. Chem. Soc.* 112, 1253 (1990), and Iyer et al., *J. Org. Chem.* 55, 4693 (1990) gave the thiophosphoramidates VII and VIII (90:10, 81% yield) (isomer ratio based on $^{31}$P-NMR. The NMR and mass spectral features were as follows: VII, $^{31}$P-NMR (CDCl$_3$) δ (ppm) 79.0; $^1$H-NMR (CDCl$_3$) δ (ppm) 0.78 (3H, d, J=6.6 Hz, —CH) 1.41 (3H, s, T-CH3) 2.55 (2H, m, H-2'), 2.70 (3H, d, $^3J_{P-H}$=12.5 Hz, —NCH$_3$), 3.36 (1H, dd, J=10.5, 2.3 Hz, H-5'), 3.56 (1H, dd, J=10.5, 2.2 Hz, H-5') 3.76 (1H, ddq, J =6.6, 6.1 $^3J_{P-H}$=12.3 Hz, H-4), 3.78 (6H, s, —OCH$_3$), 4.28 (1H, m, H-4'), 5.57 (1H, m, H-3'), 5.62 (1H, dd, J=6.1 Hz, $^3J_{P-H(5)}$=2.8 Hz, H-5), 6.48 (1H, dd, j=9.0, 5.6 Hz, H-1'), 6.85 (4H, m, -Ph), 7.26 (14H, m, -Ph), 7.62 (1H, s, H-6) 8.90 (1H, s, —NH). FAB-MS (m/z) 769, C$_4$,H$_{44}$N$_3$O$_8$PS.

The predominant isomer, VII (which is easily separated from VIII by flash chromatography), has been assigned the configuration indicated. The assignment of configurations for VII and VIII is based on the generally accepted notion that P(III) oxidations proceed with high stereoselectivity and with overall retention of configuration. E.g., Beaucage and Iyer, *Tetrahedron* 48, 2223 (1992), and Bentrude et al., *J. Am. Chem. Soc.* 111, 3981 (1989).

Example 2

Synthesis of Nucleotide Dimers Using Diastereomerically Enriched Monomer Synthons Having obtained the nucleoside phosphoramidite III in preparative-scale reactions, the stage was set for its use in solid-phase coupling with CPG-bound nucleoside. Thus, contacting a solution of III in acetonitrile with CPG-T (10 mmol) for a period of two minutes in the presence of tetrazole as an activator followed by oxidation with the thiolsulfonate resulted in efficient formation of the phosphorothioate dinucleoside with a coupling efficiency of greater than 95% (as evaluated by "trityl yields"). Iyer et al., *J. Am. Chem. Soc.*, supra, and Iyer et al., *J. Org. Chem.*, supra. Following synthesis, the CPG-bound product was heated with aqueous ammonium hydroxide (28%, 55° CH, 1 hr). Examination of the products by reverse-phase HPLC revealed that the dinucleoside phosphorothioate had been formed as a mixture of diastereomers (R$_p$:S$_p$, 40:60). Interestingly, the commonly used cyanoethylphosphate deprotection strategy (28% aq. NH$_4$OH, 55° C.) was found to be sufficient to cleave the chiral phosphate appendage in the phosphite and generate the phosphorothioate. The lack of high stereoselectivity in the formation of is consistent with other reports wherein epimerization of the phosphorous center (in the case of stereoisomerically pure phosphoramidites) is observed when acidic type activators, e.g., tetrazole, are used in conjunction with phosphoramidite methodology in the synthesis of deoxyribonucleoside phosphorothioates. SteCH, supra, and Beaucage, supra.

Example 3

Synthesis and Purification of Oligonucleotides

Oligonucleotides are synthesized on a 1 mmol scale following the standard protocol by using an automated synthesizer (e.g., Millipore 8700 DNA Synthesizer, Bedford, Mass.). Where a predominantly R$_p$ configuration is desired, the phosphoramidite III is used by dissolving it in dry acetonitrile at a concentration of 50 mg/ml. For phosphorothioate oligonucleotides, the iodine oxidation step is replaced by sulfurization with 3H-1,2-benzodithiol-3-one-1,1-dioxide (Beaucage reagent). Iyer et al., *J. Org. Chem.* 55, 4693 (1990). Two-hour treatment with ammonium hydroxide at room temperature is carried out to cleave the oligomer from the support and to deprotect in nucleoside bases. Oligonucleotides are purified by reverse-phase HPLC and/or PAGE, and desalted by using C-1 SEP-PAK cartridges.

Example 4

Stereoselective Synthesis of a Mononucleotide Phosphorothioate

Treatment of VII and VIII with sodium methoxide in methanol at ambient temperature overnight followed by heating with NH$_4$OH (28% NH$_4$OH for 1–2 hr at 55° C. gave the phosphorothioate in 90% yield with moderate to high stereoselectivity (as monitored by $^{31}$P-NMR and HPLC). The R$_p$:S$_p$ ratio of the phosphorothioate obtained from VII was 70:30, whereas the ratio of isomers obtained from VIII was 10:90. Configurations were assigned using the criteria reported for dinucleoside phosphorothioates by Iyer et al., *Bioorg. Med. Chem. Lett.* 4, 2471 (1994).

Example 5

Stereospecific Phosphorothioate Synthesis

Diazabicyclononane (DBU) (296 mg, 1.95 mmol) is dissolved in anhydrous THF (1.5 ml) and added to 3'-O-t-butyl dimethylsilyl thymidine (46 mg, 0.129 mmol) at 0° C. for 20 minutes. This solution is added slowly to the solution of VII (50 mg, 0.065 mmol) and the contents stirred for 30 minutes at room temperature. The reaction mixture is allowed to warm to room temperature and stirred for 12 h. The solution is evaporated to remove solvent and treated with ammonium hydroxide (28%, 1 ml) and heated for 4 h at 55° C. The solution is evaporated to dryness. Chromatographic purification affords 45 mg (80% yield) of 5'-O-DMT-3'-O-TBDMS TT dimer with R$_p$:S$_p$ ratio of 70:30.

Example 6

Synthesis of Monomer Synthon L (S)-pyrrolidin-2-ylmethanol was reacted with PCl$_3$ at −78° C. in the presence of triethylamine for 12 h to give the P-chloro-oxazaphospholidine LI as a colorless liquid following vacuum distillation (77.5° C., at 0.2 mm Hg). $^{31}$P NMR of 5 revealed a singlet at δ 178 ppm, representing a single isomer. From considerations of anomeric, steric, and electronic effects, the p-stereochemistry of LI could be tentatively assigned as indicated above, in which the chlorine atom was pseudoaxially disposed at the face opposite to the prolinol ring.

The reaction of LI with 5'-O-dimethoxytrityl thymidine in the presence of N,N-diusopropylethylamine for 6 h at 78° C. gave the nucleoside L as a single diastereomer. Following work up, examination of the crude product confirmed the presence of a single isomer as revealed by TLC and $^{31}$P NMR (δ 151.8 ppm). In analogy with substitution reactions of P-chloro-oxazaphospholidines involving carbon-, oxygen-, and nitrogen-based nucleophiles (Sum et al., *J. Chem. Soc. Perkin Trans. I*, 3183 (1994); Carey et al., *J. Chem. Soc. Perkin Trans I*, 831 (1993)), which gave substitution products with overall retention of configuration, L could be formulated as having the structure with S$_p$ configuration. The oxazaphospholidine L was obtained as a white solid after work up, and stored at 0 to −5° C. until ready to use.

Example 7

Solid-Phase Oligonucleotide Synthesis with Monomer L

Compound L from Example 6 was next used in solid-phase synthesis using CPG-bound nucleoside. Initially, the manual coupling mode was employed in which an acetonitrile solution of L was contacted with CPG-T for 5 to 10 min at room temperature in the presence of 1 H-tetrazole. After washing to remove the excess reagents, the resulting dinucleoside phosphite was sulfurized with 3H-1,2-benzodithiole-3-one-1,1-dioxide (2% in CH$_3$CN). Following capping, washing, and removal of the DMT group, the CPG-bound product was heated with aqueous ammonium hydroxide (28%, 65° C., 12 h). Although we do not wish to be bound by any theory, the deprotection of the phosphate appendage could follow the sequence shown below:

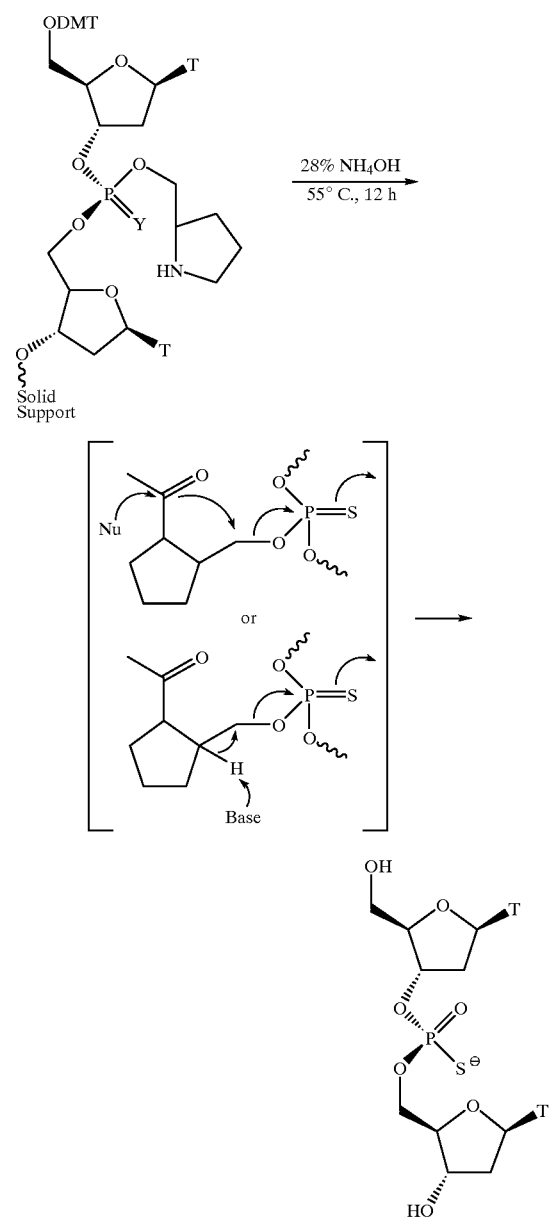

Examination of the crude product by HPLC and $^{31}$P NMR revealed the predominant formation of the S$_p$ isomer of the TpsT dimer in greater than 90% selectivity (S$_p$:R$_p$, 9:1) (configurations were assigned as described previously, Iyer et al. *Bioorg. Med. Chem. Lett.* 4, 2471 (1994)) and coupling efficiency greater than 97%.

The TpsT dimer was then prepared using the standard 1 and 10 μmol coupling program. Again, both $^{31}$P NMR and HPLC revealed the predominant formation of the $S_p$ isomer. In a parallel run, the oxazapholidine derived from (R)(+)-2-pyrrolidine methanol (D-prolinol) gave the predominant formation of $[R_p]$ TpsT ($S_p$:$R_p$, 1:9). Studies with oxazapholidines derived from A, C, and G nucleosides also revealed similar stereoselectivity in the coupling reactions.

We claim:

1. A monomer synthon for the synthesis of oligonucleotides, the monomer synthon having the general structure:

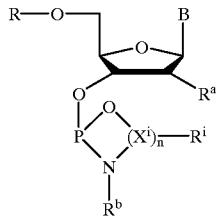

wherein $R^a$ and each $R^i$ other than $R^1$ are independently H or a $C_1$–$C_{20}$ alkyl, aryl, heterocyclyl, alkoxyalkoxy or alkoxy group, $R^b$ and $R^1$ are independently a divalent $C_1$–$C_{20}$ alkyl, alkoxyalkoxy or alkoxy group, R is a protecting group, n is 1, 2, or 3, i is from 1 to n, $X^i$ is CH, O, S, or N, provided that if n is 3 then (a) $X^2$ is optionally O, S or N, (b) $X^1$ and $X^3$ are CH, and (c) there is no $R^2$ when $X^2$ is O or S, and when n>1 the identity of each $X^i$ is independent of the identity of every other $X^i$ and the identity of each substituent $R^i$ is independent of every other $R^i$, each $R^i$ is covalently bound to the corresponding $X^i$, the $X^i$ are arranged consecutively such that $X^1$ is bound to the N and $X^n$ is bound to the O to form an n+3 membered ring, and each chiral $X^i$ is predominantly in a single stereoconfiguration, $R^b$, the N to which it is bonded, $X^1$ and $R^1$ form a five-membered heterocyclic ring, and B is any suitably protected modified or unmodified purine or pyrimidine base.

2. The monomer synthon according to claim 1, wherein n is 2, $R^b$ is $(CH_2)_2$, $X^1$ and $X^2$ are CH, $R^1$ is $CH_2$, $R^2$ is H, and having the structure:

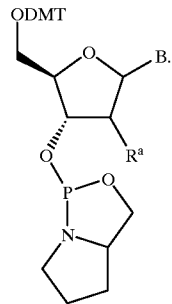

3. The monomer synthon according to claim 2, wherein $R^a$ is H or methoxy.

4. A monomer synthon for the synthesis of oligonucleotides, the monomer synthon having the general structure:

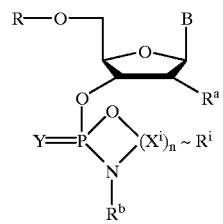

wherein

Y is sulfur or an isotope of oxygen, $R^a$ and each $R^i$ other than $R^1$ are independently H or a $C_1$–$C_{20}$ alkyl, aryl, heterocyclyl, alkoxyalkoxy or alkoxy group, $R^b$ and $R^1$ are independently a divalent $C_1$–$C_{20}$ alkyl, alkoxyalkoxy or alkoxy group, R is a protecting group, n is 1, 2, or 3, i is from 1 to n, $X^i$ is CH, O, S, or N, provided that if n is 3 then (a) $X^2$ is optionally O, S or N, (b) $X^1$ and $X^3$ are CH, and (c) there is no $R^2$ when $X^2$ is O or S, and when n>1 the identity of each $X^i$ (i.e., each of $X^1$ . . . $X^n$) is independent of the identity of every other $X^i$ and the identity of each substituent $R^i$ (i.e., each of $R^1$ . . . $R^n$) is independent of every other $R^i$, each $R^i$ is covalently bound to the corresponding $X^i$ (e.g., $X^1$–$R^1$ . . . $X^n$–$R^n$), the $X^i$ are arranged consecutively such that $X^i$ is bound to the N and $X^n$ is bound to the O to form an n+3 membered ring, each chiral $X^i$ is predominantly in a single stereoconfiguration, $R^b$, the N to which it is bonded, $X^1$ and $R^1$ form a five-membered heterocyclic ring, and B is any suitably protected modified or unmodified purine or pyrimidine base.

5. The monomer synthon according to claim 4, wherein Y is S.

6. The monomer synthon according to claim 4, wherein n is 2, $R^b$ is $(CH_2)_2$, $X^1$ and $X^2$ are CH, $R^1$ is $CH_2$, $R^2$ is H, and having the structure:

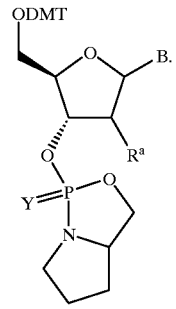

7. The monomer synthon according to claim 6, wherein Y is S.

8. The monomer synthon according to claim 7, wherein $R^a$ is H or methoxy.

9. A method of synthesizing the monomer synthon according to claim 1, comprising contacting a compound having the structure formula:

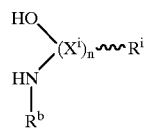

wherein each $R^i$ other than $R^1$ is independently H or a $C_1$–$C_{20}$ alkyl, aryl, heterocyclyl, alkoxyalkoxy or alkoxy group, $R^b$ and $R^1$ are independently a divalent $C_1$–$C_{20}$ alkyl, alkoxyalkoxy or alkoxy group, n is 1, 2, or 3, i is from 1 to n, $X^i$ is CH, O, S, or N, provided that if n is 3 then (a) $X^2$ is optionally O, S or N, (b) $X^1$ and $X^3$ are CH, and (c) there is no $R^2$ when $X^2$ is O or S, and when n>1 the identity of each $X^i$ is independent of the identity of every other $X^i$ and the identity of each substituent $R^i$ is independent of every other $R^i$, each $R^i$ is covalently bound to the corresponding $X^i$, the $X^i$ are arranged consecutively such that $X^1$ is bound to the N and $X^n$ is bound to the O to form an n+3 membered ring, each chiral $X^i$ is predominantly in a single stereoconfiguration, and $R^b$, the N to which it is bonded, $X^1$ and $R^1$ form a five-membered heterocyclic ring, with $PCl_3$ and reacting the product thereby formed with a nucleoside having a protected 5' hydroxyl and unprotected 3' hydroxyl.

10. The method according to claim 9, wherein n is 2, $R^b$ is $(CH_2)_n$, $X^1$ and $X^2$ are CH, $R^1$ is $CH_2$ and $R^2$ is H and $R^b$, the N to which it is bonded, $X^1$ and $R^1$ form a five-membered ring.

11. The method according to claim 10, wherein $R^a$ is H or methoxy.

12. A method of synthesizing a monomer synthon, comprising contacting the compound according to claim 1 with an oxidizing agent for oxidation of the phosphorous atom.

13. The method according to claim 12, wherein the oxidizing agent is a thiolative oxidizing agent.

14. The method according to claim 13, wherein the oxidizing agent is 3H-1,2-benzodithiol-3-one-1,1-dioxide.

15. A method of synthesizing a monomer synthon, comprising contacting the compound according to claim 2 with an oxidizing agent for oxidation of the phosphorous atom.

16. The method according to claim 15, wherein said oxidizing agent is a thiolative oxidizing agent.

17. The method according to claim 16, wherein the oxidizing agent is 3H-1,2-benzodithiol-3-one-1,1-dioxide.

18. A method of synthesizing a monomer synthon, comprising contacting the compound according to claim 3 with an oxidizing agent for oxidation of the phosphorous atom.

19. The method according to claim 18, wherein said oxidizing agent is a thiolative oxidizing agent.

20. The method according to claim 19, wherein the oxidizing agent is 3H-1,2-benzodithiol-3-one-1,1-dioxide.

* * * * *